United States Patent
Akin et al.

(10) Patent No.: US 7,912,735 B1
(45) Date of Patent: Mar. 22, 2011

(54) METHOD AND SYSTEM FOR ELIGIBLE HEALTH CARE EXPENSE IDENTIFICATION

(75) Inventors: Muhammet Serdar Akin, Santa Clara, CA (US); Daniel W. Beck, San Francisco, CA (US)

(73) Assignee: Intuit Inc., Mountain View, CA (US)

( * ) Notice: Subject to any disclaimer, the term of this patent is extended or adjusted under 35 U.S.C. 154(b) by 837 days.

(21) Appl. No.: 11/740,545

(22) Filed: Apr. 26, 2007

(51) Int. Cl.
G06Q 10/00 (2006.01)
G06Q 50/00 (2006.01)
G06Q 40/00 (2006.01)

(52) U.S. Cl. ................ 705/2; 705/3; 705/4

(58) Field of Classification Search .......... 705/2–4, 705/7
See application file for complete search history.

(56) References Cited

U.S. PATENT DOCUMENTS

| | | | |
|---|---|---|---|
| 6,208,973 B1 * | 3/2001 | Boyer et al. | 705/2 |
| 7,380,707 B1 * | 6/2008 | Fredman | 235/379 |
| 2007/0219828 A1 * | 9/2007 | Schlicher et al. | 705/2 |

OTHER PUBLICATIONS

Curb healthcare expenses when employees take ownership, May 2005, The National Provisioner's Meat & Deli Retailer, vol. 4 No. 4.*

* cited by examiner

*Primary Examiner* — Luke Gilligan
(74) *Attorney, Agent, or Firm* — Gunnison, McKay & Hodgson, L.L.P.; Philip McKay

(57) ABSTRACT

A method and system for eligible health care expense identification includes a process for eligible health care expense identification whereby electronic data including data representing health care expense transactions for a defined time frame is accessed. Electronic data representing rules defining eligible health care expenses is then obtained. The electronic data is then analyzed using the electronic data representing the rules defining eligible health care expenses to identify health care expense transactions that are potentially eligible for reimbursement from a health care expense account and/or a tax deduction. A user is then notified of the identified health care expense transactions.

5 Claims, 2 Drawing Sheets

METHOD AND SYSTEM FOR ELIGIBLE HEALTH CARE EXPENSE IDENTIFICATION

BACKGROUND

Currently, many health care related expenses are either directly tax deductible or can be paid with "pre-tax" dollars using one or more health care expense account programs.

In many cases, specific health care expenses are directly tax deductible. As one example, typically, if the accumulated health care expenses for a given year exceed a defined percentage of the employee's/taxpayer's income, the healthcare expenses are deductible. However, to claim this deduction, the employee/taxpayer must keep track of all health care expenses and determine which healthcare expenses are considered "legitimate" health care expenses by the IRS or other government tax agency. For many employees/taxpayers, keeping track of these expenses is too burdensome and therefore valid tax deductions are never claimed because the employee/taxpayer lacks the proper tracking and documentation and/or does not consider the deduction worth the considerable effort needed to keep these records.

In addition to direct tax deductions, health care expense account programs can also provide a taxpayer with tax relief for some health care expense. Currently, many employers offer health care expense account programs in addition to traditional health care insurance. Herein, health care expense account programs are defined as programs which provide an employee/taxpayer and/or employee/taxpayer dependents a designated health care expense account that is assigned to the employee/taxpayer and is used to reimburse the employee/taxpayer for defined eligible health care expenses incurred by the employee/taxpayer and/or the employee's/taxpayer's dependents. Examples of currently available health care expense account programs include, but are not limited to: flexible spending accounts (FSAs); health care reimbursement arrangements (HRAs); and health care spending accounts (HSAs).

In many cases, the health care expense account is a virtual account maintained by a health care expense program administrator or management service, also called a program administrator, either under the direct control of the employer or as a third-party agent of the employer. In other cases, the health care expense account is set up by the employees/taxpayers themselves. Typically, health care expense accounts are funded by either by the employee/taxpayer and/or the employer.

Health care expense account programs typically help the employee/taxpayer pay health care expenses that are not covered by the employee's/taxpayer's health care insurance such as: deductibles; the employee's/taxpayer's portion of health care expenses; co-payments for doctors visits and prescriptions; co-payments for medical supplies and devices; extended care and/or home care; and various other health care expenses determined to be eligible by the employer and/or health care expense program administrator and/or the IRS.

In typical operation, funds are deposited in the health care expense account by the employee/taxpayer, the employer, or a combination of both. Once the health care expense account is funded, the funds are made available to reimburse the employee/taxpayer for out of pocket expenses incurred by the employee/taxpayer in eligible health care expense transactions. In most cases, the employee/taxpayer first pays the health care expense using his or her own funds. Then the employee/taxpayer must identify the transaction, provide documentation for the transaction, and make a request to the program administrator for reimbursement of the funds.

The process above sounds simple enough and represents a genuine effort on the part of the government and employers to help employees/taxpayers afford quality health care. However, as noted above, in reality, the process of keeping track of numerous eligible health care expenses on a day-to-day, transaction-to-transaction, basis often becomes too burdensome for many employees/taxpayers and, in many cases, the employee/taxpayer simply chooses not to claim a healthcare expense deduction and/or participate in the health care expense account program. This is especially true since, in many cases, individual eligible health care expenses are often only a few dollars, such as a $10.00 co-pay for a doctor visit or prescription. However, in many cases, large numbers of individual eligible health care expenses are incurred by the employee/taxpayer and/or the employee's/taxpayer's dependents over the course of a year and these sums go unclaimed because the employee/taxpayer does not recognize the cumulative effect of numerous relatively small payments over the course of a year. As a result, well meaning deduction and reimbursement programs intended as "benefits" come to be viewed by the employee/taxpayer as "burdensome" at best, and often as simply irrelevant. This fact serves neither the employee/taxpayer nor the employer's/government's best interests.

SUMMARY

In accordance with one embodiment, a method and system for eligible health care expense identification includes a process for eligible health care expense identification whereby electronic data including data representing health care expense transactions over a defined time frame is collected. The electronic data is then analyzed and health care expense transactions that are potentially eligible for reimbursement from a health care expense account are identified. The identified health care expense transactions are then verified as eligible health care expense transactions based on the electronic data collected and/or known/programmed rules defining eligible health care expenses.

In one embodiment, the electronic data including data representing health care expense transactions is collected from electronic transaction data maintained by banks and/or other financial institutions. In one embodiment, the electronic data including data representing health care expense transactions is collected from electronic transaction data maintained by credit account providers, such as credit card companies.

In one embodiment, the electronic data including data representing health care expense transactions is collected by interfacing with a computing system implemented process such as, but not limited too, a computing system implemented personal financial management system, a computing system implemented personal accounting system, and/or a computing system implemented healthcare expense management system.

In one embodiment, the electronic data including data representing health care expense transactions is collected from electronically transferred Explanation of Benefits (EOB) data provided by health insurance providers. In one embodiment, the electronic data including data representing health care expense transactions is collected from the employee/user by the employee/user scanning paper forms of verification such as bills, receipts, EOBs, etc. in to a computing system and then electronically transferring the data.

In one embodiment, the electronic data including data representing health care expense transactions is collected through electronically transferred invoices/patient bills provided by health care providers. In one embodiment, the electronic data including data representing health care expense transactions is collected from electronic receipts provided by suppliers of medications and/or medical devices and/or supplies.

In one embodiment, the electronic data including data representing health care expense transactions is collected by manual data entry by a user through a user interface device. In one embodiment, the electronic data including data representing health care expense transactions is collected from any combination of the above sources and/or from any other source of electronic data including data representing health care expense transactions, whether known at the time of filing or as developed thereafter.

In one embodiment, once the electronic data is collected, the data is then analyzed and compared with using known eligibility rules to identify potentially eligible health care expense transactions.

In one embodiment electronic transaction data maintained by banks and/or credit account providers is obtained and analyzed using the known eligibility rules to identify potential health care expense transactions and based on an assigned category of transaction and/or the merchant paid through the transaction and the known/programmed rules for eligible health care expenses. In one embodiment, the electronic transaction data maintained by banks and/or credit account providers is analyzed to identify potential health care expense transactions and/or verify the eligible health care expense transactions based on "level-3" transaction data identifying specific items purchased, the provider of such items, the date of purchase, the price paid by the employee, and the known/programmed rules for eligible health care expenses. In one embodiment, the electronic receipts provided by suppliers of medications and/or medical devices/supplies, such as drug stores, pharmacies, medical supply companies, etc., are obtained and analyzed to identify potential health care expense transactions. In one embodiment, the health care expense transactions are then verified based on receipt data identifying specific items purchased, the date of purchase, the provider of such items, the price paid by the employee, and the known/programmed rules for eligible health care expenses.

In one embodiment, the electronic data including data representing health care expense transactions is analyzed and eligible health care expense transactions are identified by any combination of the methods described above and/or any other method of scanning and/or analyzing electronic data to identify eligible health care expense transactions, whether known at the time of filing or as developed thereafter.

In one embodiment, eligible health care expense transactions are further verified by checking the subject matter and/or purchase items associated with the health care expense transactions against a listing of eligible (or non-eligible) health care expenses. In one embodiment, the listing of eligible (or non-eligible) health care expenses is provided by the employer and/or program administrator and/or a government tax agency.

In one embodiment, once the electronic transaction data is obtained and analyzed to identify potentially eligible health care expense transactions, the user is then notified of these potentially eligible health care expense transactions.

In one embodiment, eligible health care expense transactions are also identified and/or authorized by the employee. In this embodiment, the employee is provided a listing of potentially eligible health care expense transactions. The employee is then provided an opportunity to edit the list and/or remove specific potentially eligible health care expense transactions from the listing prior to submission to the program administrator for reimbursement and/or claiming a tax deduction.

Using the method and system for eligible health care expense identification disclosed herein, an employee's/taxpayer's financial transaction records for a defined period are automatically analyzed in light of known eligibility rules and potentially deductible and/or eligible health care expense transactions are automatically identified for the employee/taxpayer. As a result, the employee/taxpayer is, to a large extent, relieved of the burden of identifying and tracking individual health care expenses. Consequently, the employee/taxpayer is more likely to use the health care expense deduction/program and receive the full intended benefit of these programs.

In one embodiment in addition to analyzing current transactions, i.e., transactions from the current tax/program year, the method and system for eligible health care expense identification disclosed herein can be used to analyze historical transactions, i.e., transactions from previous tax/program years. In this way, the method and system for eligible health care expense identification disclosed herein can be used to identify potentially deductible and/or eligible health care expense transactions that were either ignored and/or forfeited in the past, and, in some cases, can be claimed via an amended tax return or retroactive benefit claim. In addition, the historical transaction data can be used to more accurately determine how many pre-tax dollars should be placed in a health care expense account program and/or determine future tax liabilities. Consequently, using one embodiment of the method and system for eligible health care expense identification disclosed herein, the employee/taxpayer can, at a minimum, be made aware of the potential tax benefits he or she is forfeiting, thereby allowing the employee/taxpayer to at least make an informed decision as whether or not to take a deduction and/or participate in a health care expense program.

As discussed in more detail below, using the below embodiments, with little or no modification and/or user input, there is considerable flexibility, adaptability, and opportunity for customization to meet the specific needs of various users under numerous circumstances.

Figure 1:
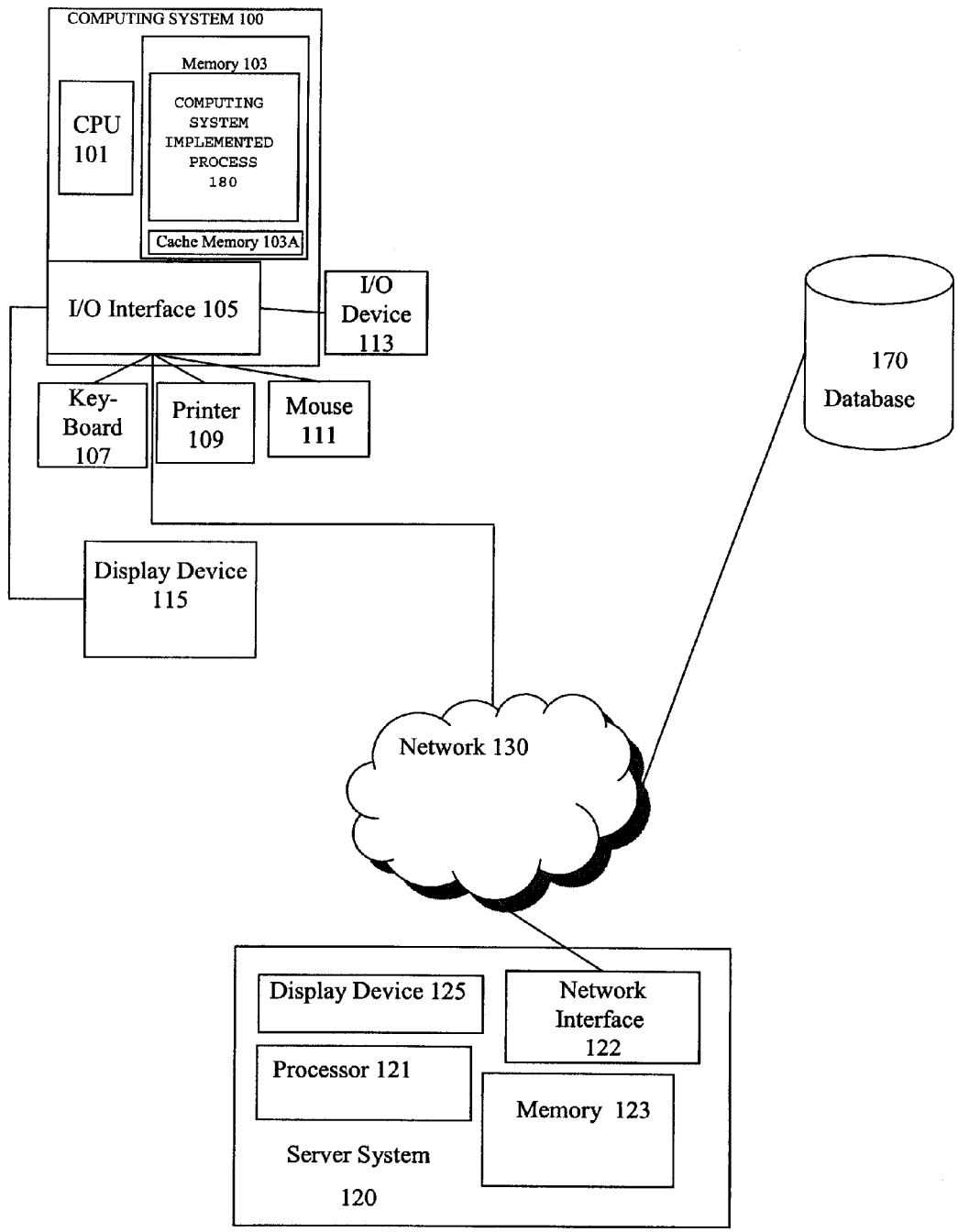
FIG. 1 is a block diagram of an exemplary hardware architecture for implementing one embodiment.

Common reference numerals are used throughout the FIGS. and the detailed description to indicate like elements. One skilled in the art will readily recognize that the above FIGS. are examples and that other architectures, modes of operation, orders of operation and elements/functions can be provided and implemented without departing from the characteristics and features of the invention, as set forth in the claims.

DETAILED DESCRIPTION

Embodiments will now be discussed with reference to the accompanying FIGS., which depict one or more exemplary embodiments. Embodiments may be embodied in many different forms and should not be construed as limited to the embodiments set forth herein, shown in the FIGS., and/or described below. Rather, these exemplary embodiments are provided to allow a complete disclosure that conveys the principles of the invention, as set forth in the claims, to those of skill in the art.

In accordance with one embodiment, a method and system for eligible health care expense identification includes a process for eligible health care expense identification whereby electronic data including data representing health care expense transactions over a defined time frame is collected. The electronic data is then analyzed and health care expense transactions that are potentially eligible for reimbursement from a health care expense account are identified. The identified health care expense transactions are then verified as eligible health care expense transactions based on the electronic data collected and/or known/programmed rules defining eligible health care expenses.

In one embodiment, the electronic data including data representing health care expense transactions is collected from electronic transaction data maintained by banks and/or other financial institutions. In one embodiment, the electronic data including data representing health care expense transactions is collected from electronic transaction data maintained by credit account providers, such as credit card companies.

In one embodiment, the electronic data including data representing health care expense transactions is collected by interfacing with a computing system implemented process such as, but not limited too, a computing system implemented personal financial management system, a computing system implemented personal accounting system, and/or a computing system implemented healthcare expense management system.

In one embodiment, the electronic data including data representing health care expense transactions is collected from electronically transferred Explanation of Benefits (EOB) data provided by health insurance providers. In one embodiment, the electronic data including data representing health care expense transactions is collected from the employee/user by the employee/user scanning paper forms of verification such as bills, receipts, EOBs, etc. in to a computing system and then electronically transferring the data.

In one embodiment, the electronic data including data representing health care expense transactions is collected through electronically transferred invoices/patient bills provided by health care providers. In one embodiment, the electronic data including data representing health care expense transactions is collected from electronic receipts provided by suppliers of medications and/or medical devices and/or supplies.

In one embodiment, the electronic data including data representing health care expense transactions is collected by manual data entry by a user through a user interface device. In one embodiment, the electronic data including data representing health care expense transactions is collected from any combination of the above sources and/or from any other source of electronic data including data representing health care expense transactions, whether known at the time of filing or as developed thereafter.

In one embodiment, once the electronic data is collected, the data is then analyzed and compared with using known eligibility rules to identify potentially eligible health care expense transactions.

In one embodiment electronic transaction data maintained by banks and/or credit account providers is obtained and analyzed using the known eligibility rules to identify potential health care expense transactions and based on an assigned category of transaction and/or the merchant paid through the transaction and the known/programmed rules for eligible health care expenses. In one embodiment, the electronic transaction data maintained by banks and/or credit account providers is analyzed to identify potential health care expense transactions and/or verify the eligible health care expense transactions based on "level-3" transaction data identifying specific items purchased, the provider of such items, the date of purchase, the price paid by the employee, and the known/programmed rules for eligible health care expenses. In one embodiment, the electronic receipts provided by suppliers of medications and/or medical devices/supplies, such as drug stores, pharmacies, medical supply companies, etc., are obtained and analyzed to identify potential health care expense transactions. In one embodiment, the health care expense transactions are then verified based on receipt data identifying specific items purchased, the date of purchase, the provider of such items, the price paid by the employee, and the known/programmed rules for eligible health care expenses.

In one embodiment, the electronic data including data representing health care expense transactions is analyzed and eligible health care expense transactions are identified by any combination of the methods described above and/or any other method of scanning and/or analyzing electronic data to identify eligible health care expense transactions, whether known at the time of filing or as developed thereafter.

In one embodiment, eligible health care expense transactions are further verified by checking the subject matter and/or purchase items associated with the health care expense transactions against a listing of eligible (or non-eligible) health care expenses. In one embodiment, the listing of eligible (or non-eligible) health care expenses is provided by the employer and/or program administrator and/or a government tax agency.

In one embodiment, once the electronic transaction data is obtained and analyzed to identify potentially eligible health care expense transactions, the user is then notified of these potentially eligible health care expense transactions.

In one embodiment, eligible health care expense transactions are also identified and/or authorized by the employee. In this embodiment, the employee is provided a listing of potentially eligible health care expense transactions. The employee is then provided an opportunity to edit the list and/or remove specific potentially eligible health care expense transactions from the listing prior to submission to the program administrator for reimbursement and/or claiming a tax deduction.

Using the method and system for eligible health care expense identification disclosed herein, an employee's/taxpayer's financial transaction records for a defined period are automatically analyzed in light of known eligibility rules and potentially deductible and/or eligible health care expense transactions are automatically identified for the employee/taxpayer. As a result, the employee/taxpayer is, to a large extent, relieved of the burden of identifying and tracking individual health care expenses. Consequently, the employee/taxpayer is more likely to use the health care expense deduction/program and receive the full intended benefit of these programs.

In addition, in one embodiment, the method and system for eligible health care expense identification disclosed herein can be used to analyze historical transactions, i.e., transactions from previous tax/program years. In this way, the method and system for eligible health care expense identification disclosed herein can be used to identify potentially deductible and/or eligible health care expense transactions that were either ignored and/or forfeited in the past, and, in some cases, can be claimed via an amended tax return or retroactive benefit claim. Consequently, using one embodiment of the method and system for eligible health care expense identification disclosed herein, the employee/taxpayer can, at a minimum, be made aware of the potential tax benefits he or she is forfeiting, thereby allowing the employee/taxpayer to at least make an informed decision as to whether or not to take a deduction and/or participate in a health care expense program.

As discussed in more detail below, using the below embodiments, with little or no modification and/or user input, there is considerable flexibility, adaptability, and opportunity for customization to meet the specific needs of various users under numerous circumstances.

Some embodiments are implemented in a computing system including a conventional computing system running a conventional operating system such as those distributed by Microsoft Corporation of Redmond Wash.; Apple Computer Inc. of Cupertino Calif.; any Unix operating system; any Linux operating system; the Palm OS series of operating systems; or any other operating system designed to generally manage operations on a computing system, whether known at the time of filing or as developed later. Some embodiments are implemented in a mobile computing system running mobile operating systems such as Symbian® OS, Windows® Mobile, or any other operating system designed to generally manage operations on a mobile computing system, whether known at the time of filing or as developed later. As described more fully below, embodiments can be implemented on computing systems other than a conventional computing system such as, for example, a personal digital assistant, a cell phone, or other computing system capable of processing computer readable data, whether known at the time of filing or as developed later. Computing systems also include those in which one or more computing resources (hardware or software) are located remotely and accessed via network, such as a Local Area Network (LAN), Wide Area Network (WAN), a public network, such as the Internet, a private network, a combination of network types, a computing system bus, or other electronic medium in which data may be exchanged between one computing system and one or more other computing system(s), whether known at the time of filing or as developed later. Embodiments may be included as add-on software for existing software programs, packages or applications, and embodiments may be a feature of an application that is bundled with a computing system or sold separately. Some embodiments may also be implemented as functionality embedded in hardware devices and systems.

Output generated by one or more embodiments can be displayed on a display screen, transmitted to a remote device, stored on any database, computer server or other storage mechanism, printed, or used in any other way. In addition, in some embodiments, processes and/or systems described herein may make use of input provided to the computer device implementing a process and/or application, discussed herein, via user interface devices such as a keyboard, mouse, touchpad, or any other device capable of providing user input to a computing system or for translating user actions into computing system operations, whether known at the time of filing or as developed later.

Hardware System Architecture

FIG. 1 is a block diagram of exemplary hardware architecture for implementing one embodiment of a process for eligible health care expense identification, such as exemplary processes for eligible health care expense identification 200, discussed below, that includes: a computing system 100; a server system 120; and a database 170, all operatively connected by a network 130.

As seen in FIG. 1, computing system 100 typically includes a processor 101, an input/output (I/O) interface 105, and a memory system 103, including cache memory 103A. In one embodiment, computing system 100 includes all or part of one or more computing system implemented processes 180 such as, but not limited to, a computing system implemented personal financial management system, a computing system implemented personal accounting system, and/or a computing system implemented healthcare expense management system that is a used by, is a parent system for, is accessed by, and/or is otherwise associated with, a process for eligible health care expense identification, such as exemplary processes for eligible health care expense identification 200

Computing system 100 may further include standard user interface devices such as a keyboard 107, a mouse 111, a printer 109, and a display device 115, as well as, one or more standard input/output (I/O) devices 113, such as a compact disk (CD) or DVD drive, floppy disk drive, or other digital or waveform port, or other device capable of inputting data to, and outputting data from, computing system 100, whether known at the time of filing or as later developed. As discussed in more detail below, in one embodiment, a process for eligible health care expense identification, and/or one or more computing system implemented processes, can be loaded, in whole, or in part, into computing system 100 via I/O device 113, such as from a CD, DVD or floppy disk containing all, or part, of a process for eligible health care expense identification and/or a computing system implemented process.

Also shown in FIG. 1 is database 170. In one embodiment, database 170 is a designated server system or computing system, or a designated portion of a server system or computing system, such as computing systems 100 and 120. In one embodiment, database 170 is a dedicated mass storage device implemented in software, hardware, or a combination of hardware and software. In one embodiment, database 170 is a web-based function. As discussed in more detail below, in one embodiment, a process for eligible health care expense identification, and/or one or more computing system implemented processes, is/are stored in whole, or in part, in database 170.

In one embodiment, computing system 100 and database 170, are coupled to a server system 120 by network 130. Server system 120 typically includes a server system display device 125, a server system processor 121, a server system memory 123, and a server system network interface 122. As discussed in more detail below, in one embodiment, a process for eligible health care expense identification, and/or one or more computing system implemented processes, is/are stored in whole, or in part, in server system 120.

Network 130 can be any network or network system that is of interest to a user such as a Local Area Network (LAN), a Wide Area Network (WAN), a public network, such as the Internet, a private network, a combination of network types, or other network capable of allowing communication between two or more computing systems, whether known at the time of filing or as later developed. In various embodiments, server system network interface 122 and I/O interface 105 include analog modems, digital modems, a network interface card, a broadband connection, or any other means for communicably coupling computing system 100, database 170, and server system 120, via network 130, whether known at the time of filing or as later developed.

Those of skill in the art will readily recognize that the components shown in FIG. 1, such as computing system 100, database 170, server system 120, and their respective components, are shown for illustrative purposes only and that architectures with more or fewer components can implement, and benefit from, a process for eligible health care expense identification, such as exemplary process for eligible health care expense identification 200 discussed below. Moreover, one or more components of computing system 100, database 170, and server system 120 may be located remotely from their respective system and accessed via a network, as discussed herein. In addition, the particular type of, and configuration of, computing systems 100, database 170, and server system 120 are not relevant.

As discussed in more detail below, in one embodiment, a process for eligible health care expense identification, and/or one or more computing system implemented processes, is/are stored in whole, or in part, in memory system 103 and/or cache memory 103A, of computing system 100, and/or in server memory system 123 of server system 120 and/or in database 170, and executed on computing system 100. As used herein, a memory refers to a volatile memory, a non-volatile memory, or any combination of the two.

Although a process for eligible health care expense identification, and/or one or more computing system implemented processes, can sometimes be referred to herein, alternatively, as a process, an application, a module, a program, a component of a software system, a component of a software package, a component of a parent system, or a feature of a parent system, this terminology is illustrative only. In some embodiments, a process for eligible health care expense identification, and/or one or more computing system implemented processes, is/are capable of being called from an application or the operating system. In one embodiment, an application or program is generally defined to be any executable code. Moreover, those of skill in the art will understand that when it is said that an application or an operation takes some action, the action is the result of executing one or more instructions by a processor, such as processor 101 or server system processor 121. In one embodiment, execution of a process for eligible health care expense identification, and/or one or more computing system implemented processes, by processor 101 or server system processor 121, results in the operations of an agent computer process (not shown) and/or a rule computer process (not shown).

In one embodiment, a process for eligible health care expense identification, and/or one or more computing system implemented processes, is/are a computer application or process implemented and/or run and/or stored, in full, or in part, in, or on, a computer program product. Herein, a computer program product comprises a medium configured to store and/or transport computer readable code, whether known at the time of filing or as later developed. Some examples of computer program products are CD-ROM discs, DVDs, ROM cards, floppy discs, magnetic tapes, computer hard drives, servers on a network, such as server system 120 of FIG. 1, and signals transmitted over a network, such as network 130 of FIG. 1, or other media or process capable of delivering computer readable data representing computer readable code, whether known at the time of filing or as later developed. This medium may belong to a computing system, such as computing system 100 of FIG. 1, described above. However, the medium also may be removed from the computing system.

For example, all, or part, of a process for eligible health care expense identification, and/or one or more computing system implemented processes, may be stored in a memory that is physically located in a location, such as server system memory 123, or database 170, of FIG. 1, different from a computing system, such as computing system 100 of FIG. 1, utilizing a process for eligible health care expense identification, and/or one or more computing system implemented processes. In one embodiment, all, or part, of a process for eligible health care expense identification, and/or one or more computing system implemented processes, may be stored in a memory that is physically located, separate from the computing system's processor(s), such as processor 101 of FIG. 1, and the computing system processor(s) can be coupled to the memory in a client-server system, such as server system 120 of FIG. 1, or, alternatively, via connection to another computer, such as computing system 100 of FIG. 1, via modems and analog lines, digital interfaces and a digital carrier line, or wireless or cellular connections.

In one embodiment, the computing systems and/or server system, such as computing system 100 and/or server system 120 of FIG. 1, running and/or utilizing and/or storing all, or part, of a process for eligible health care expense identification, and/or one or more computing system implemented processes, is a portable computer, a workstation, a two-way pager, a cellular telephone, a smart phone, a digital wireless telephone, a personal digital assistant, a server computer, an Internet appliance, or any other device that includes components that can execute all, or part, of a process for eligible health care expense identification, and/or one or more computing system implemented processes, in accordance with at least one of the embodiments as described herein. Similarly, in another embodiment, a process for eligible health care expense identification, and/or one or more computing system implemented processes, is/are implemented on and/or run and/or stored on a computing system and/or server system that is comprised of multiple different computers, wireless devices, cellular telephones, digital telephones, two-way pagers, personal digital assistants, server computers, or any desired combination of these devices, that are interconnected to perform the processes as described herein.

Process

Herein, the terms "beneficiary", "employee", "taxpayer", "employee/taxpayer", "user", and/or "consumer" are used interchangeably to denote the potential, or actual, beneficiary of a tax deduction and/or beneficiary of a health care expense account program and/or the beneficiary's dependents and/or designated agent of the beneficiary.

Herein, the term "government", "governmental agency", "tax agency", "government tax agency" and/or "governmental tax agency" are used interchangeably to denote any federal, state, local, or other regulatory and/or revenue collection agency responsible for establishing tax rules and/or enforcing those rules and/or collecting taxes.

Herein, the term "employer" is used to denote the party offering the health care expense account program as a benefit to the "employee". Herein, the terms "program administrator", "program manager", "health care expense account program administrator", and/or "health care expense account program manager" are used interchangeably to denote the party charged with administrating, processing, and making payments associated with reimbursement requests from the "employee".

In accordance with one embodiment, a method and system for eligible health care expense identification includes a process for eligible health care expense identification whereby electronic data including data representing health care expense transactions for a defined time frame is collected. The electronic data is then analyzed and compared with known eligibility rules to identify health care expense transactions that are potentially eligible for reimbursement from a health care expense account and/or a tax deduction. The identified health care expense transactions are then brought to the attention of the user.

Figure 2:
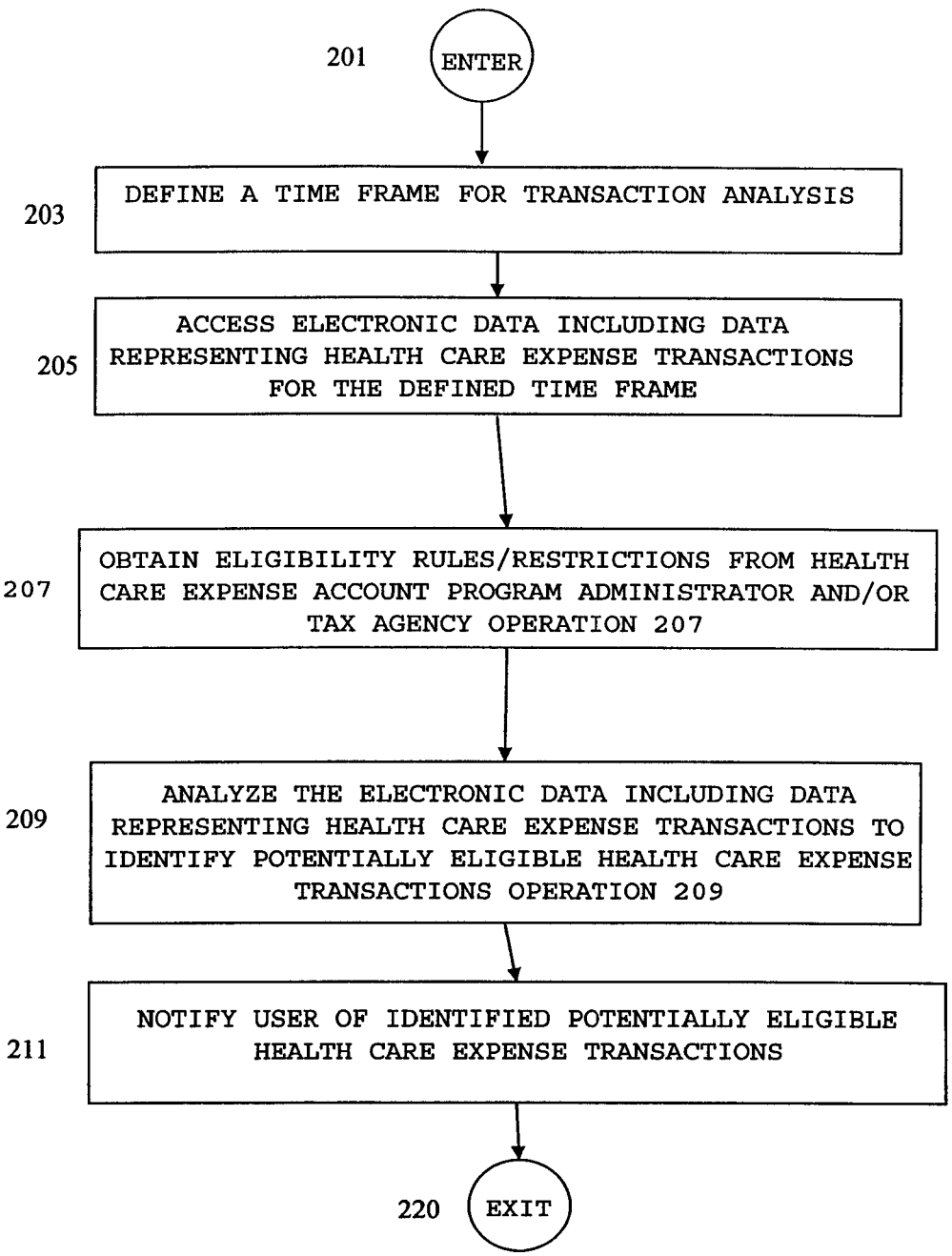
FIG. 2 is a flow chart depicting a process for eligible health care expense identification in accordance with one embodiment.

FIG. 2 a flow chart depicting a process for eligible health care expense identification 200 in accordance with one embodiment. Process for eligible health care expense identification 200 begins at ENTER OPERATION 201 of FIG. 2 and process flow proceeds to DEFINE A TIME FRAME FOR TRANSACTION ANALYSIS OPERATION 203.

In one embodiment, at DEFINE A TIME FRAME FOR TRANSACTION ANALYSIS OPERATION 203 a user defines a time frame for which an analysis of transactions is to be conducted using process for eligible health care expense identification 200.

In one embodiment, the time frame of DEFINE A TIME FRAME FOR TRANSACTION ANALYSIS OPERATION 203 is defined by the user of process for eligible health care expense identification 200. In one embodiment, the time frame is set as a default value by the provider of process for eligible health care expense identification 200 with, in one embodiment, a user override feature.

In one embodiment, the timeframe of DEFINE A TIME FRAME FOR TRANSACTION ANALYSIS OPERATION 203 is set to coincide with a tax year, health care expense account year, and/or a calendar year. In one embodiment, the time frame can be set to shorter periods such as, but not limited to: six months; a quarter; a month; a fortnight; a week; a day; or any other time frame desired by the user of process for eligible health care expense identification 200 and/or the provider of process for eligible health care expense identification 200.

In one embodiment, the timeframe of DEFINE A TIME FRAME FOR TRANSACTION ANALYSIS OPERATION 203 is set to periods longer than a year. In one embodiment, the time frame of DEFINE A TIME FRAME FOR TRANSACTION ANALYSIS OPERATION 203 is set as specific historical dates, such as, but not limited to: a specified year before the present year; a specified historical quarter; a specified historical month; etc. As discussed in more detail herein, this historical application/analysis feature of process for eligible health care expense identification 200 can be used to analyze historical transactions to identify potentially deductible and/or eligible health care expense transactions that were either ignored and/or forfeited in the past, and, in some cases, can be claimed via an amended tax return or retroactive benefit claim. In one embodiment, this historical application/ analysis feature of process for eligible health care expense identification 200 can be used to gather accurate data regarding pervious healthcare expenses and then this data can be used to predict future health care expenses accurately. In one embodiment, these predictions are then used to help a user determine how much money should be placed in health care spending account or help the user determine what the user's tax liability may be.

In one embodiment, the time frame of DEFINE A TIME FRAME FOR TRANSACTION ANALYSIS OPERATION 203 is set by user establishing/defining start and end dates for the analysis of process for eligible health care expense identification 200 using a user interface device, such as a keyboard, mouse, touch pad, voice recognition software, or any other means and/or mechanism for converting user actions into computing system processes. This allows the user to set any time frame desired at DEFINE A TIME FRAME FOR TRANSACTION ANALYSIS OPERATION 203.

In one embodiment, once the time frame is established at DEFINE A TIME FRAME FOR TRANSACTION ANALYSIS OPERATION 203, process flow proceeds to ACCESS ELECTRONIC DATA INCLUDING DATA REPRESENTING HEALTH CARE EXPENSE TRANSACTIONS FOR THE DEFINED TIME FRAME OPERATION 205.

In one embodiment, at ACCESS ELECTRONIC DATA INCLUDING DATA REPRESENTING HEALTH CARE EXPENSE TRANSACTIONS FOR THE DEFINED TIME FRAME OPERATION 205, electronic data including data representing health care expense transactions is accessed/ collected from one or more sources.

In one embodiment, the electronic data including data representing health care expense transactions is collected from electronic transaction data maintained by banks and/or credit account providers, including credit card companies. In one embodiment, access to the electronic data including data representing health care expense transactions is obtained from banks and/or credit account providers in the form of historical payment/transaction data, typically in electronic format, using one of numerous methods known to those of skill in the art.

In one embodiment, the historical payment/transaction data is obtained from a financial institution, such as a bank or credit union, credit card account provider, using the Open Financial Exchange (OFX) specification. OFX is a specification for the electronic exchange of financial data between financial institutions, businesses, consumers, and other users and user processes, such as process for eligible health care expense identification 200, or a parent system implementing process for eligible health care expense identification 200, such as computing system implemented process 180 of FIG. 1, via the Internet. OFX was created in early 1997 and is well known to those of skill in the art. OFX supports a wide range of financial activities including consumer and small business banking, consumer and small business bill payment, bill presentment, payment history displays, and investments tracking, including stocks, bonds, mutual funds, 401(k), and bank account details. OFX enables transactional, permissive, data feed driven Web sites, such as bank websites, thin clients, and financial software systems, to operate and communicate, easily, seamlessly and securely. Consequently, in one embodiment, using OFX, historical payment/transaction data can be made readily available to process for eligible health care expense identification 200 (FIG. 2) and/or a parent system implementing process for eligible health care expense identification 200 at ACCESS ELECTRONIC DATA INCLUDING DATA REPRESENTING HEALTH CARE EXPENSE TRANSACTIONS FOR THE DEFINED TIME FRAME OPERATION 205.

As noted, the OFX specification is well known to those of skill in the art and is publicly available for implementation by any financial institution or vendor. As of March 2004, OFX is supported by over 2000 banks and brokerages as well as major payroll processing companies.

In one embodiment, the historical payment/transaction data is obtained from a financial institution, such as a bank, credit card provider, or credit union, using any other method for accessing the historical payment/transaction data, including manual entry of the data. In one embodiment, process for eligible health care expense identification 200 is part of a parent personal health expense management, personal financial, business financial, accounting, or tax preparation software system, program, package or application, such as computing system implemented process 180 of FIG. 1, that implements, includes, is accessed by, and/or is otherwise associated with, a process for eligible health care expense identification, such as process for eligible health care expense identification 200, as one of multiple features. Some of these parent systems, have the capability to gather payment data, often using OFX, and then store the data for use by process for eligible health care expense identification 200 in one of numerous locations by one of numerous methods known to those of skill in the art.

As noted above, several methods for obtaining historical payment/transaction data including data representing health care expense transactions from electronic transaction data maintained by banks and/or credit account providers are well known to those of skill in the art. Consequently, these various methods for obtaining historical payment data are not discussed further herein to avoid detracting from the disclosure.

In one embodiment, the electronic data including data representing health care expense transactions is collected from electronic receipts provided by suppliers of medications and/or medical devices and/or supplies. According to one embodiment, the suppliers transfer electronic copies of the receipts, often in specific formats, to the provider of process for eligible health care expense identification 200. As noted above, in one embodiment, process for eligible health care expense identification 200 is part of a parent personal health expense management, personal financial, business financial, accounting, or tax preparation software system, program, package or application, such as computing system implemented process 180 of FIG. 1, that implements, includes, is accessed by, and/or is otherwise associated with, a process for eligible health care expense identification, such as process for eligible health care expense identification 200, as one of multiple features. Some of these parent systems, provide the capability to obtain, receive, and/or process electronic copies of the receipts, often in their specific formats, and then store the data for use by process for eligible health care expense identification 200 in one of numerous locations by one of numerous methods known to those of skill in the art.

Returning to FIG. 2, in one embodiment, the electronic data including data representing health care expense transactions is accessed/collected at ACCESS ELECTRONIC DATA INCLUDING DATA REPRESENTING HEALTH CARE EXPENSE TRANSACTIONS FOR THE DEFINED TIME FRAME OPERATION 205 through electronically transferred invoices/patient bills and/or claim data provided to process for eligible health care expense identification 200 by health care providers such as hospitals and/or doctors and/or other medical service personnel.

Invoices submitted to the patient/employee by the health care providers, such as hospitals and/or doctors typically include total cost billed as well as the expected patient/employee's share of that cost. In addition, copies of clams made to the health insurance providers often include this same information.

According to one embodiment, the health care providers transfer electronic copies of the invoices/claims, often in specific formats, to the provider of process for eligible health care expense identification 200. As noted above, in one embodiment, process for eligible health care expense identification 200 is part of a parent personal health expense management, personal financial, business financial, accounting, or tax preparation software system, program, package or application, such as computing system implemented process 180 of FIG. 1, that implements, includes, is accessed by, and/or is otherwise associated with, a process for eligible health care expense identification, such as process for eligible health care expense identification 200, as one of multiple features. Some of these parent systems, provide the capability to obtain, receive, and/or process electronic copies of the invoices/claims, often in their specific formats, and then store the data for use by process for eligible health care expense identification 200 in one of numerous locations by one of numerous methods known to those of skill in the art.

In one embodiment, electronic data including data representing health care expense transactions is collected/accessed at ACCESS ELECTRONIC DATA INCLUDING DATA REPRESENTING HEALTH CARE EXPENSE TRANSACTIONS FOR THE DEFINED TIME FRAME OPERATION 205 from electronically transferred Explanation of Benefits (EOB) data provided to process for eligible health care expense identification 200 by a health insurance provider and/or the user of process for eligible health care expense identification 200.

As required by law, EOBs are forms that health insurance providers send insured parties for each benefit claim made by either the insured or the health care provider on behalf of the insured. EOBs include various types of information but typically include: information as to the amount of a given claim; information as to the amount paid by the health insurance provider on a given claim; information regarding any amounts not paid on a given claim by the health insurance provider, and why the amounts were not paid; and information regarding any amounts not paid on a given claim by the health insurance provider that it is the responsibility of the insured, or the responsible insured party, i.e., the employee/taxpayer, to pay.

According to one embodiment, the health insurance providers transfer electronic copies of the EOBs, often in specific formats, to the provider of process for eligible health care expense identification 200. As noted above, in one embodiment, process for eligible health care expense identification 200 is part of a parent personal health expense management, personal financial, business financial, accounting, or tax preparation software system, program, package or application, such as computing system implemented process 180 of FIG. 1, that implements, includes, is accessed by, and/or is otherwise associated with, a process for eligible health care expense identification, such as process for eligible health care expense identification 200, as one of multiple features. Some of these parent systems, provide the capability to obtain, receive, and/or process electronic copies of the EOBs and then store the data for use by process for eligible health care expense identification 200 in one of numerous locations by one of numerous methods known to those of skill in the art.

In some embodiments, the electronic data including data representing health care expense transactions is accessed/collected at ACCESS ELECTRONIC DATA INCLUDING DATA REPRESENTING HEALTH CARE EXPENSE TRANSACTIONS FOR THE DEFINED TIME FRAME OPERATION 205 from any combination of the above sources and/or from any other source of electronic data including data representing health care expense transactions, whether known at the time of filing or as developed thereafter.

In one embodiment, the electronic data including data representing health care expense transactions accessed/collected at ACCESS ELECTRONIC DATA INCLUDING DATA REPRESENTING HEALTH CARE EXPENSE TRANSACTIONS FOR THE DEFINED TIME FRAME OPERATION 205 is stored, in whole, or in part, in a database maintained by, accessible by, owned by, or otherwise related to, a provider of process for eligible health care expense identification 200 by any one of the numerous mechanisms known to those of skill in the art. For instance, in one embodiment, the data, in whole, or in part, is stored in a memory system, such as memory system 103 or server memory system 123, or database 170, of FIG. 1, or in a cache memory, such as cache memory 103A of FIG. 1, or in any main memory or mass memory, associated with a computing device, such as computing system 100 described above. In one embodiment, the data, in whole, or in part, is stored in any computing device and/or server system, such as computing system 100 or server system 120, or other device, in another location, or on/in a computer readable medium, and/or any other computer program product, as defined herein. In one embodiment, the data, in whole, or in part, is stored on a webpage, in a web-based system or on a public network such as the Internet.

Returning to FIG. 2, in some embodiments, the data stored as described above is maintained, in whole, or in part, by: the provider of process for eligible health care expense identification 200; a health care spending account administrator; a health insurance provider; a third party data storage institution; any third party service or institution; or any other parties. In these embodiments, access to the electronic data including data representing health care expense transactions is then granted to the provider of process for eligible health care expense identification 200 at ACCESS ELECTRONIC DATA INCLUDING DATA REPRESENTING HEALTH CARE EXPENSE TRANSACTIONS FOR THE DEFINED TIME FRAME OPERATION 205 by providing access to the data and/or providing the data on a computer program product.

In other embodiments, the electronic data including data representing health care expense transactions is provided through a network of computing systems and/or server systems that is comprised of multiple different computers, wireless devices, cellular telephones, digital telephones, two-way pagers, personal digital assistants, server computers, or any desired combination of these devices, that are interconnected using a network, such as network 130 of FIG. 1. As discussed above, network 130 can be any network or network system that is of interest to a user such as a Local Area Network (LAN), a Wide Area Network (WAN), a public network, such as the Internet, a private network, a combination of network types, or other network capable of allowing communication between two or more computing systems, whether available or known at the time of filing or as later developed.

In other embodiments, the electronic data including data representing health care expense transactions is accessed/collected through e-mail or through text messaging. In other embodiments, the electronic data including data representing health care expense transactions is provided to process for eligible health care expense identification 200 through any method, apparatus, process or mechanism for transferring data and/or text from one or more devices, computing systems, server systems, databases, web site/web functions and/or any devices having a data storage capability to one or more other devices, computing systems, server systems, databases, web site/web functions and/or any devices having a data storage capability, whether known at the time of filing or as thereafter developed.

In one embodiment, once the electronic data including data representing health care expense transactions is accessed/collected at ACCESS ELECTRONIC DATA INCLUDING DATA REPRESENTING HEALTH CARE EXPENSE TRANSACTIONS FOR THE DEFINED TIME FRAME OPERATION 205 process flow proceeds to OBTAIN ELIGIBILITY RULES/RESTRICTIONS FROM HEALTH CARE EXPENSE ACCOUNT PROGRAM ADMINISTRATOR AND/OR TAX AGENCY OPERATION 207.

In one embodiment, at OBTAIN ELIGIBILITY RULES/RESTRICTIONS FROM HEALTH CARE EXPENSE ACCOUNT PROGRAM ADMINISTRATOR AND/OR TAX AGENCY OPERATION 207 rules and/or requirements defining eligible health care expenses are obtained from any source including, but not limited to: an employer providing a health care expense account program; a health care expense account program administrator; statue; a government agency; a private agency; any public or private third party agencies and/or institutions; or any other source of health care expense account eligibility rules and/or federal, state or local tax laws/rules.

In one embodiment, the rules and/or requirements defining eligible health care expenses are dictated by federal, state or local tax and/or regulatory statutes. As discussed above, in many cases, specific health care expenses are directly tax deductible. As one example, if the accumulated health care expenses for a given year exceed a defined percentage of the employee's/taxpayer's income, the healthcare expenses are often deductible. However, to claim this deduction, the employee/taxpayer must keep track of all health care expenses and determine which healthcare expenses are considered "legitimate" health care expenses by the IRS or other government tax agency. In these cases, the rules and/or requirements defining eligible health care expenses are dictated by federal, state and/or local tax statute and the rules provided at OBTAIN ELIGIBILITY RULES/RESTRICTIONS FROM HEALTH CARE EXPENSE ACCOUNT PROGRAM ADMINISTRATOR AND/OR TAX AGENCY OPERATION 207 would include any threshold percentages along with a listing or guideline of typically eligible health care expenses and/or a specific listing of eligible health care expenses.

As also discussed above, in many instances an employer offers a health care expense account program to the employee. As noted above, health care expense account programs are defined as programs which provide an employee and/or employee dependents a designated health care expense account that is assigned to the employee and is used to reimburse the employee for defined eligible health care expenses.

As also noted above, in many cases, the health care expense account is a virtual account maintained by a health care expense program administrator or management service, also called a program administrator, either under the direct control of the employer or as a third-party agent of the employer. In other cases, the health care expense account is set up by the employees themselves. Typically, health care expense accounts are funded by either the employee and/or the employer using pre-tax dollars.

As discussed above, health care expense account programs typically are designed to help the employee pay health care expenses that are not covered by the employee's health care insurance. Examples of health care expenses that are typically eligible for reimbursement under a health care expense account program include, but are not limited to: health care insurance deductibles; the employee's portion of health care expenses; co-payments for doctors visits and prescriptions; co-payments for medical supplies and devices; extended care and/or home care; and various other health care expenses determined to be eligible by the employer and/or health care expense program administrator.

In operation, funds are typically deposited in the health care expense account by the employee, the employer, or a combination of both. Once the health care expense account is funded, the funds are made available to reimburse the employee for out of pocket expenses incurred by the employee in eligible health care expense transactions. In most cases, the employee first pays the health care expense using his or her own funds. Then the employee makes a request to a program administrator for reimbursement of the funds. The employee is then reimbursed for his or her out of pocket expenses from the health care expense account.

Examples of common health care expense account programs currently available include, but are not limited to: flexible spending accounts (FSAs); health care reimbursement arrangements (HRAs); and health care spending accounts (HSAs). Each of these health care expense account programs operate to reimburse the employee for out of pocket expenses incurred by the employee in eligible health care expense transactions. However, the funding, lifespan, and portability of these three programs vary.

For instance, in a typical flexible spending account (FSA) program the employee must elect to deposit a specified pre-tax dollar amount in the health care expense account, i.e., the FSA, to cover health care expenses that will occur over a predefined future period. For instance, as one example, the employee must elect to deposit a pre-tax dollar amount specified by the employee to be paid into the health care expense account for pre-tax reimbursement of all eligible health care expenses to be incurred in the next 12 months. In many cases, the amount specified by the employee is paid by deducting a portion of the specified amount from the employee's compensation over multiple pay periods. In other cases, the employer makes contributions to the FSA and the employer deposits funds in the health care expense account on a periodic basis.

Using a typical FSA, it is important that an employee predict his or her total eligible health care expenses fairly accurately. This is because any funds not used to reimburse the employee for a transaction occurring within the pre-defined period, i.e., unused funds, are typically forfeited. Consequently, an underestimate of the employee's total eligible health care expenses results in "real" post tax expense while an overestimate of the total eligible health care expenses results in forfeited pre-tax money. FSAs are the most common form of health care expense account programs. Given the forfeiture feature of the typical FSA, timely and accurate submission of reimbursement requests is critical.

A typical health care reimbursement arrangement (HRA) is very similar to an FSA except that the HRA account is typically funded by the employer and, in many cases, the health care expense account balance remains for employee to use as long as the employee is employed by the employer.

Health care spending accounts (HSAs) are a federal program whereby a user and/or employer funds the health care spending account themselves with pre-tax dollars. The user then reimburses himself or herself from the account for eligible health care expenses. A health care spending account remains the property of the user for life. However, funds drawn from the health care spending account prior to the defined retirement age must be identified, accounted for, and verified through special tax documentation.

Each of the health care expense account programs discussed above, includes specific eligibility rules that, in one embodiment, are obtained at OBTAIN ELIGIBILITY RULES/RESTRICTIONS FROM HEALTH CARE EXPENSE ACCOUNT PROGRAM ADMINISTRATOR AND/OR TAX AGENCY OPERATION 207.

In addition, in one embodiment, an itemized listing of eligible (or non-eligible) health care expenses is provided to process for eligible health care expense identification 200 by the employer and/or program administrator and/or tax agency at OBTAIN ELIGIBILITY RULES/RESTRICTIONS FROM HEALTH CARE EXPENSE ACCOUNT PROGRAM ADMINISTRATOR AND/OR TAX AGENCY OPERATION 207. As an example, the employer and/or program administrator may specifically exclude certain treatments, types of treatments, medications, types of medications and/or procedures from being eligible health care expenses under the health care expense account program. In one embodiment, this listing of eligible (or non-eligible) health care expenses is provided to process for eligible health care expense identification 200 by manual data entry at OBTAIN ELIGIBILITY RULES/RESTRICTIONS FROM HEALTH CARE EXPENSE ACCOUNT PROGRAM ADMINISTRATOR AND/OR TAX AGENCY OPERATION 207.

Those of skill in the art will recognize that any health care expense account program, whether it be an FSA, an HRA, an HSA, or any other health care expense account-type program and/or tax deduction program known at the time of filing or as developed thereafter, can be used with, and benefit from, the processes for eligible health care expense identification disclosed herein.

In one embodiment, at OBTAIN ELIGIBILITY RULES/RESTRICTIONS FROM HEALTH CARE EXPENSE ACCOUNT PROGRAM ADMINISTRATOR AND/OR TAX AGENCY OPERATION 207 the rules and/or requirements defining eligible health care expenses are obtained by manual entry by the user and/or the provider of process for eligible health care expense identification 200 and/or any agents thereof.

In one embodiment, at OBTAIN ELIGIBILITY RULES/RESTRICTIONS FROM HEALTH CARE EXPENSE ACCOUNT PROGRAM ADMINISTRATOR AND/OR TAX AGENCY OPERATION 207 data representing the rules and/or requirements defining eligible health care expenses is stored, in whole, or in part, in a database maintained by, accessible by, owned by, or otherwise related to, a provider of process for eligible health care expense identification 200 and/or the health care expense account program provider by any one of the numerous mechanisms known to those of skill in the art. For instance, in one embodiment, the data, in whole, or in part, is stored in a memory system, such as memory system 103 or server memory system 123, or database 170, of FIG. 1, or in a cache memory, such as cache memory 103A of FIG. 1, or in any main memory or mass memory, associated with a computing device, such as computing system 100 described above. In one embodiment, the data, in whole, or in part, is stored in any computing device and/or server system, such as computing system 100 or server system 120, or other device, in another location, or on/in a computer readable medium, and/or any other computer program product, as defined herein. In one embodiment, the data, in whole, or in part, is stored on a webpage, in a web-based system or on a public network such as the Internet. Returning to FIG. 2, in some embodiments, the data stored as described above is maintained, in whole, or in part, by: the provider of process for eligible health care expense identification 200; a health care expense account administrator; a health insurance provider; a third party data storage institution; any third party service or institution; or any other parties.

In these embodiments, access to the data representing the rules and/or requirements defining eligible health care expenses is then granted to the provider of process for eligible health care expense identification 200 at ACCESS ELECTRONIC DATA INCLUDING DATA REPRESENTING HEALTH CARE EXPENSE TRANSACTIONS FOR THE DEFINED TIME FRAME OPERATION 205 by providing access to the data and/or providing the data on a computer program product.

In other embodiments, the electronic data representing the rules and/or requirements defining eligible health care expenses is provided through a network of computing systems and/or server systems that is comprised of multiple different computers, wireless devices, cellular telephones, digital telephones, two-way pagers, personal digital assistants, server computers, or any desired combination of these devices, that are interconnected using a network, such as network 130 of FIG. 1. As discussed above, network 130 can be any network or network system that is of interest to a user such as a Local Area Network (LAN), a Wide Area Network (WAN), a public network, such as the Internet, a private network, a combination of network types, or other network capable of allowing communication between two or more computing systems, whether available or known at the time of filing or as later developed.

In other embodiments, the data representing the rules and/or requirements defining eligible health care expenses is provided through e-mail or through text messaging. In other embodiments, the data representing the rules and/or requirements defining eligible health care expenses is provided to process for eligible health care expense identification 200 at OBTAIN ELIGIBILITY RULES/RESTRICTIONS FROM HEALTH CARE EXPENSE ACCOUNT PROGRAM ADMINISTRATOR AND/OR TAX AGENCY OPERATION 207 through any method, apparatus, process or mechanism for transferring data and/or text from one or more devices, computing systems, server systems, databases, web site/web functions and/or any devices having a data storage capability to one or more other devices, computing systems, server systems, databases, web site/web functions and/or any devices having a data storage capability, whether known at the time of filing or as thereafter developed.

In one embodiment, once the rules and/or requirements defining eligible health care expenses are obtained at OBTAIN ELIGIBILITY RULES/RESTRICTIONS FROM HEALTH CARE EXPENSE ACCOUNT PROGRAM ADMINISTRATOR AND/OR TAX AGENCY OPERATION 207, process flow proceeds to ANALYZE THE ELECTRONIC DATA INCLUDING DATA REPRESENTING HEALTH CARE EXPENSE TRANSACTIONS TO IDENTIFY POTENTIALLY ELIGIBLE HEALTH CARE EXPENSE TRANSACTIONS OPERATION 209.

In one embodiment, at ANALYZE THE ELECTRONIC DATA INCLUDING DATA REPRESENTING HEALTH CARE EXPENSE TRANSACTIONS TO IDENTIFY POTENTIALLY ELIGIBLE HEALTH CARE EXPENSE TRANSACTIONS OPERATION 209, the electronic data including data representing health care expense transactions accessed/collected at ACCESS ELECTRONIC DATA INCLUDING DATA REPRESENTING HEALTH CARE EXPENSE TRANSACTIONS FOR THE DEFINED TIME FRAME OPERATION 205, for the time frame identified at DEFINE A TIME FRAME FOR TRANSACTION ANALYSIS OPERATION 203, is analyzed using the rules and/or requirements defining eligible health care expenses obtained at OBTAIN ELIGIBILITY RULES/RESTRICTIONS FROM HEALTH CARE EXPENSE ACCOUNT PROGRAM ADMINISTRATOR AND/OR TAX AGENCY OPERATION 207 to identify specific health care expense transactions potentially eligible for reimbursement and/or deduction.

In one embodiment, the electronic transaction data maintained by banks and/or credit account providers obtained at ACCESS ELECTRONIC DATA INCLUDING DATA REPRESENTING HEALTH CARE EXPENSE TRANSACTIONS FOR THE DEFINED TIME FRAME OPERATION 205 for the time frame identified at DEFINE A TIME FRAME FOR TRANSACTION ANALYSIS OPERATION 203 is analyzed at ANALYZE THE ELECTRONIC DATA INCLUDING DATA REPRESENTING HEALTH CARE EXPENSE TRANSACTIONS TO IDENTIFY POTENTIALLY ELIGIBLE HEALTH CARE EXPENSE TRANSACTIONS OPERATION 209 to identify potential health care expense transactions based on an assigned category of the transaction and/or the merchant paid through the transaction. In one embodiment, the electronic transaction data maintained by banks and/or credit account providers is analyzed to identify potential health care expense transactions using "level-3" transaction data.

Level-3 transaction data refers to the ability to process detailed purchase information with the financial transaction. The supplemental information associated with level-3 transaction data typically includes data elements such as a customer/employee code, invoice and service order number, part number, item description, quantity, unit of measure, unit price, etc. Using level-3 data, transactional details are provided that allow a determination as to exactly what was purchased and, in this instance, if the item and/or service purchased represents an eligible health care expense. Consequently, in one embodiment, level-3 data is used to both identify and verify eligible health care expense transactions from electronic transaction data maintained by banks and/or credit account providers.

In one embodiment, the electronic receipts provided by suppliers of medications and/or medical devices/supplies at ACCESS ELECTRONIC DATA INCLUDING DATA REPRESENTING HEALTH CARE EXPENSE TRANSACTIONS FOR THE DEFINED TIME FRAME OPERATION 205, for the time frame identified at DEFINE A TIME FRAME FOR TRANSACTION ANALYSIS OPERATION 203, is analyzed at ANALYZE THE ELECTRONIC DATA INCLUDING DATA REPRESENTING HEALTH CARE EXPENSE TRANSACTIONS TO IDENTIFY POTENTIALLY ELIGIBLE HEALTH CARE EXPENSE TRANSACTIONS OPERATION 209 using the seller and the item description on the receipt, i.e., the data identifying specific items purchased, the date of purchase, and the price paid by the employee/taxpayer.

In one embodiment, the electronically transferred invoices/patient bills provided by health care providers at ACCESS ELECTRONIC DATA INCLUDING DATA REPRESENTING HEALTH CARE EXPENSE TRANSACTIONS FOR THE DEFINED TIME FRAME OPERATION 205, for the time frame identified at DEFINE A TIME FRAME FOR TRANSACTION ANALYSIS OPERATION 203, is analyzed at ANALYZE THE ELECTRONIC DATA INCLUDING DATA REPRESENTING HEALTH CARE EXPENSE TRANSACTIONS TO IDENTIFY POTENTIALLY ELIGIBLE HEALTH CARE EXPENSE TRANSACTIONS OPERATION 209 to identify the amount billed directly to the employee by the health care providers. In one embodiment, the eligible health care expense transactions are then considered verified based again on the source of the data.

In one embodiment, the electronically transferred EOB data provided by health insurance providers at ACCESS ELECTRONIC DATA INCLUDING DATA REPRESENTING HEALTH CARE EXPENSE TRANSACTIONS FOR THE DEFINED TIME FRAME OPERATION 205, for the time frame identified at DEFINE A TIME FRAME FOR TRANSACTION ANALYSIS OPERATION 203, is analyzed at ANALYZE THE ELECTRONIC DATA INCLUDING DATA REPRESENTING HEALTH CARE EXPENSE TRANSACTIONS TO IDENTIFY POTENTIALLY ELIGIBLE HEALTH CARE EXPENSE TRANSACTIONS OPERATION 209 to identify the employee's portion of payments made to the health care provider and/or any co-payments made by the employee. In one embodiment, the eligible health care expense transactions are then considered verified based on the fact the source of the data is the health insurance provider.

In one embodiment, any electronic data including data representing health care expense transactions obtained at ACCESS ELECTRONIC DATA INCLUDING DATA REP- RESENTING HEALTH CARE EXPENSE TRANSACTIONS FOR THE DEFINED TIME FRAME OPERATION 205, for the time frame identified at DEFINE A TIME FRAME FOR TRANSACTION ANALYSIS OPERATION 203, is analyzed at ANALYZE THE ELECTRONIC DATA INCLUDING DATA REPRESENTING HEALTH CARE EXPENSE TRANSACTIONS TO IDENTIFY POTENTIALLY ELIGIBLE HEALTH CARE EXPENSE TRANSACTIONS OPERATION 209 and eligible health care expense transactions are identified at IDENTIFY ELIGIBLE HEALTH CARE EXPENSE TRANSACTIONS/VERIFY THE ELIGIBLE HEALTH CARE EXPENSE TRANSACTIONS OPERATION 209 by any combination of the methods described above and/or any other method of analyzing/scanning electronic data to identify eligible health care expense transactions, whether known at the time of filing or as developed thereafter.

In one embodiment, once the electronic data of ACCESS ELECTRONIC DATA INCLUDING DATA REPRESENTING HEALTH CARE EXPENSE TRANSACTIONS FOR THE DEFINED TIME FRAME OPERATION 205, for the time frame identified at DEFINE A TIME FRAME FOR TRANSACTION ANALYSIS OPERATION 203, is analyzed at ANALYZE THE ELECTRONIC DATA INCLUDING DATA REPRESENTING HEALTH CARE EXPENSE TRANSACTIONS TO IDENTIFY POTENTIALLY ELIGIBLE HEALTH CARE EXPENSE TRANSACTIONS OPERATION 209 process flow proceeds to NOTIFY USER OF IDENTIFIED POTENTIALLY ELIGIBLE HEALTH CARE EXPENSE TRANSACTIONS OPERATION 211.

In one embodiment, at NOTIFY USER OF IDENTIFIED POTENTIALLY ELIGIBLE HEALTH CARE EXPENSE TRANSACTIONS OPERATION 211, data representing the identified potentially eligible health care expense transactions is made available to the user of process for eligible health care expense identification 200.

In one embodiment, data representing the identified potentially eligible health care expense transactions is made available to the user by storing the data, in whole, or in part, in a database maintained by, accessible by, owned by, or otherwise related to, a provider of process for eligible health care expense identification 200 and/or provider of a health care expense account program by any one of the numerous mechanisms known to those of skill in the art. For instance, in one embodiment, the data, in whole, or in part, is stored in a memory system, such as memory system 103 or server memory system 123, or database 170, of FIG. 1, or in a cache memory, such as cache memory 103A of FIG. 1, or in any main memory or mass memory, associated with a computing device, such as computing system 100 described above. In one embodiment, the data, in whole, or in part, is stored in any computing device and/or server system, such as computing system 100 or server system 120, or other device, in another location, or on/in a computer readable medium, and/or any other computer program product, as defined herein. In one embodiment, the data, in whole, or in part, is stored on a webpage, in a web-based system or on a public network such as the Internet.

In some embodiments, the data stored as described above is maintained, in whole, or in part, by: the provider of process for eligible health care expense identification 200; the provider of the health care expense account program; a third party data storage institution; any third party service or institution; or any other parties.

Returning to FIG. 2, in these embodiments, the data representing the identified potentially eligible health care expense transactions is made available to the user, or the user's agent, by granting the user's and/or the user agent's computing system access to the data and/or providing the data on a computer program product.

In other embodiments, data representing the identified potentially eligible health care expense transactions is provided to the user, or the user's agent, through a network of computing systems and/or server systems that is comprised of multiple different computers, wireless devices, cellular telephones, digital telephones, two-way pagers, personal digital assistants, server computers, or any desired combination of these devices, that are interconnected using a network, such as network 130 of FIG. 1. As discussed above, network 130 can be any network or network system that is of interest to a user such as a Local Area Network (LAN), a Wide Area Network (WAN), a public network, such as the Internet, a private network, a combination of network types, or other network capable of allowing communication between two or more computing systems, whether available or known at the time of filing or as later developed.

Returning to FIG. 2, in other embodiments, the data representing the identified potentially eligible health care expense transactions is made available to the user, or user agent, through e-mail or through text messaging. In other embodiments, the data representing the identified potentially eligible health care expense transactions is made available to the user, or user agent, through any method, apparatus, process or mechanism for transferring data and/or text from one or more devices, computing systems, server systems, databases, web site/web functions and/or any devices having a data storage capability to one or more other devices, computing systems, server systems, databases, web site/web functions and/or any devices having a data storage capability, whether known at the time of filing or as thereafter developed.

In one embodiment, the data representing the identified potentially eligible health care expense transactions is made available to the user, or user agent, by automatically transferring the data to a user's, or user agent's, computing system and/or storage device by any of the methods and/or mechanisms discussed herein.

In one embodiment, once the data representing the identified potentially eligible health care expense transactions is transferred to the user, or user agent, process flow proceeds to EXIT OPERATION 220 and process for eligible health care expense identification 200 returns to DEFINE A TIME FRAME FOR TRANSACTION ANALYSIS OPERATION 203 to await the next cycle.

Using process for eligible health care expense identification 200, an employee's/taxpayer's financial transaction records and/or data for a defined period are automatically analyzed in light of known eligibility rules and potentially deductible and/or eligible health care expense transactions are automatically identified for the employee/taxpayer. As a result, using process for eligible health care expense identification 200, the employee/taxpayer is, to a large extent, relieved of the burden of identifying and tracking individual health care expenses. Consequently, the employee/taxpayer is more likely to use the health care expense deduction/program and receive the full intended benefit of these programs.

In addition, in one embodiment, process for eligible health care expense identification 200 can be used to analyze historical transactions, i.e., transactions from previous tax/program years. In this way, process for eligible health care expense identification 200 can be used to identify potentially deductible and/or eligible health care expense transactions that were either ignored and/or forfeited in the past, and, in some cases, can be claimed via an amended tax return or retroactive benefit claim. Consequently, using process for eligible health care expense identification 200, the employee/ taxpayer can, at a minimum, be made aware of the potential tax benefits he or she is forfeiting, thereby allowing the employee/taxpayer to at least make an informed decision as whether or not to take a deduction and/or participate in a health care expense program.

In addition, as discussed above, using many health care spending accounts, such as an FSA, it is important that an employee predict his or her total eligible health care expenses fairly accurately. This is because any funds not used to reimburse the employee for a transaction occurring within the predefined period, i.e., unused funds, are typically forfeited. Using process for eligible health care expense identification 200, and the historical transaction scan feature, a user can more accurately determine how many pre-tax dollars should be placed in a health care expense account program, such as an FSA or HRA account, and/or determine future tax liabilities.

As discussed in more detail above, using the above embodiments, with little or no modification and/or user input, there is considerable flexibility, adaptability, and opportunity for customization to meet the specific needs of various users under numerous circumstances.

The present invention has been described in particular detail with respect to specific possible embodiments. Those of skill in the art will appreciate that the invention may be practiced in other embodiments. For example, the nomenclature used for components, capitalization of component designations and terms, the attributes, data structures, or any other programming or structural aspect is not significant, mandatory, or limiting, and the mechanisms that implement the invention or its features can have various different names, formats, and/or protocols. Further, the system and/or functionality of the invention may be implemented via various combinations of software and hardware, as described, or entirely in hardware elements. Also, particular divisions of functionality between the various components described herein is merely exemplary, and not mandatory or significant. Consequently, functions performed by a single component may, in other embodiments, be performed by multiple components, and functions performed by multiple components may, in other embodiments, be performed by a single component.

Some portions of the above description present the features of the present invention in terms of algorithms and symbolic representations of operations, or algorithm-like representations, of operations on information/data. These algorithmic and/or algorithm-like descriptions and representations are the means used by those of skill in the art to most effectively and efficiently convey the substance of their work to others of skill in the art. These operations, while described functionally or logically, are understood to be implemented by computer programs and/or computing systems. Furthermore, it has also proven convenient at times to refer to these arrangements of operations as steps or modules or by functional names, without loss of generality.

Unless specifically stated otherwise, as would be apparent from the above discussion, it is appreciated that throughout the above description, discussions utilizing terms such as "defining", "accessing", "analyzing", "obtaining", "collecting", "identifying", "transferring", "storing", "notifying", etc., refer to the action and processes of a computing system or similar electronic device that manipulates and operates on data represented as physical (electronic) quantities within the computing system memories, resisters, caches or other information storage, transmission or display devices.

Certain aspects of the present invention include process steps or operations and instructions described herein in an algorithmic and/or algorithmic-like form. It should be noted that the process steps and/or operations and instructions of the present invention can be embodied in software, firmware, and/or hardware, and when embodied in software, can be downloaded to reside on and be operated from different platforms used by real time network operating systems.

The present invention also relates to an apparatus or system for performing the operations described herein. This apparatus or system may be specifically constructed for the required purposes, or the apparatus or system can comprise a general purpose system selectively activated or configured/reconfigured by a computer program stored on a computer program product as defined herein that can be accessed by a computing system or other device.

Those of skill in the art will readily recognize that the algorithms and operations presented herein are not inherently related to any particular computing system, computer architecture, computer or industry standard, or any other specific apparatus. Various general purpose systems may also be used with programs in accordance with the teaching herein, or it may prove more convenient/efficient to construct more specialized apparatuses to perform the required operations described herein. The required structure for a variety of these systems will be apparent to those of skill in the art, along with equivalent variations. In addition, the present invention is not described with reference to any particular programming language and it is appreciated that a variety of programming languages may be used to implement the teachings of the present invention as described herein, and any references to a specific language or languages are provided for illustrative purposes only and for enablement of the contemplated best mode of the invention at the time of filing.

The present invention is well suited to a wide variety of computer network systems operating over numerous topologies. Within this field, the configuration and management of large networks comprise storage devices and computers that are communicatively coupled to similar and/or dissimilar computers and storage devices over a private network, a LAN, a WAN, a private network, or a public network, such as the Internet.

It should also be noted that the language used in the specification has been principally selected for readability, clarity and instructional purposes, and may not have been selected to delineate or circumscribe the inventive subject matter. Accordingly, the disclosure of the present invention is intended to be illustrative, but not limiting, of the scope of the invention, which is set forth in the claims below.

In addition, the operations shown in the FIGS. are identified using a particular nomenclature for ease of description and understanding, but other nomenclature is often used in the art to identify equivalent operations.

Therefore, numerous variations, whether explicitly provided for by the specification or implied by the specification or not, may be implemented by one of skill in the art in view of this disclosure.

What is claimed is:

1. A system for eligible health care expense identification comprising:
   defining, by a user at a first computing system, an analysis time frame including one or more time periods in a previous tax year;
   using one or more processors to obtain historical line item financial transaction data from a bank associated with the user;

using the one or more processors to obtain electronic data from an employer of the user, the employer providing a health care expense account program, the electronic data representing rules governing the determination of health care expenses from the analysis time frame that may be eligible for a retroactive benefit claim from one or more health care expense account programs;

using the one or more processors to analyze the financial transaction data to identify any health care expenses from the analysis time frame that are potentially eligible for a retroactive benefit claim from one or more health care expense account programs but which was not claimed, using the electronic data representing the rules defining health care expenses eligible for a retroactive benefit claim; and notifying a user of any identified health care expenses from the analysis time frame that are potentially eligible for a retroactive benefit claim.

2. The system for eligible health care expense identification of claim 1, wherein;
   at least one of the health care expense account program is a flexible spending account (FSA) program.

3. The system for eligible health care expense identification of claim 1, wherein;
   at least one of the health care expense account program is a health care reimbursement arrangement (HRA) program.

4. The system for eligible health care expense identification of claim 1, wherein;
   at least one of the health care expense account program is a health care spending account (HSA) program.

5. A computer program product for eligible health care expense identification comprising:
   a nontransitory computer readable medium; and
   processor-executable code stored on the computer readable medium, which when executed by a processor performs a process for eligible health care expense identification comprising:
   defining an analysis time frame including one or more time periods in a previous tax year;
   obtaining historical line item financial transaction data from a bank associated with the user;
   obtaining electronic data from an employer of the user, the employer providing a health care expense account program, the electronic data representing rules governing the determination of health care expenses from the analysis time frame that may be eligible for a retroactive benefit claim from one or more health care expense account programs;
   analyzing the financial transaction data to identify any health care expenses from the analysis time frame that are potentially eligible for a retroactive benefit claim from one or more health care expense account programs but which was not claimed, using the electronic data representing the rules defining health care expenses eligible for a retroactive benefit claim; and
   notifying a user of any identified health care expenses from the analysis time frame that are potentially eligible for a retroactive benefit claim.

* * * * *

UNITED STATES PATENT AND TRADEMARK OFFICE
CERTIFICATE OF CORRECTION

| | | |
|---|---|---|
| PATENT NO. | : 7,912,735 B1 | Page 1 of 1 |
| APPLICATION NO. | : 11/740545 | |
| DATED | : March 22, 2011 | |
| INVENTOR(S) | : Muhammet Serdar Akin and Daniel W. Beck | |

It is certified that error appears in the above-identified patent and that said Letters Patent is hereby corrected as shown below:

Column 25, Line 21, Claim 2, replace "program" with --programs--;
Column 25, Line 25, Claim 3, replace "program" with --programs--; and
Column 25, Line 30, Claim 4, replace "program" with --programs--.

Signed and Sealed this
Second Day of October, 2012

David J. Kappos
*Director of the United States Patent and Trademark Office*